United States Patent [19]

Columbus

[11] 4,323,536
[45] Apr. 6, 1982

[54] MULTI-ANALYTE TEST DEVICE

[75] Inventor: Richard L. Columbus, Rochester, N.Y.

[73] Assignee: Eastman Kodak Company, Rochester, N.Y.

[21] Appl. No.: 118,840

[22] Filed: Feb. 6, 1980

[51] Int. Cl.³ .................... G01N 21/78; G01N 33/68; G01N 33/62
[52] U.S. Cl. ........................................ 422/56; 422/58; 422/100; 23/230 B
[58] Field of Search .............. 356/244, 246; 23/230 B, 23/230 R; 422/55, 56, 57, 58, 100, 102; 261/112

[56] References Cited

U.S. PATENT DOCUMENTS

| | | | |
|---|---|---|---|
| 3,450,393 | 6/1969 | Munters | 261/112 |
| 3,526,480 | 9/1970 | Findl et al. | |
| 3,607,090 | 9/1971 | Maxon | |
| 3,690,836 | 9/1972 | Buissiere et al. | 422/56 |
| 3,715,192 | 2/1973 | Wenz et al. | 422/56 |
| 3,905,702 | 9/1975 | Johnson | 356/246 X |
| 3,961,346 | 6/1976 | White | 356/244 |
| 3,964,871 | 6/1976 | Hochstrasser | 23/230 B X |
| 3,992,158 | 11/1976 | Przybylowicz et al. | |
| 4,088,448 | 5/1978 | Lilja et al. | 422/58 X |
| 4,233,029 | 11/1980 | Columbus | 422/55 |
| 4,248,829 | 2/1981 | Kitajima et al. | 422/56 |

FOREIGN PATENT DOCUMENTS 2934760  3/1980  Fed. Rep. of Germany .

*Primary Examiner*—Arnold Turk
*Attorney, Agent, or Firm*—Dana M. Schmidt

[57] ABSTRACT

A test device, and a method of testing, that use a plurality of test elements each for a different analyte, all elements being supplied analyte from a single quantity of liquid. The liquid is conveyed to the test elements by a capillary transport zone, and means for venting the zone are provided. To prevent contamination, liquid flow control means are included so that the liquid is confined to a plurality of flow paths each of which extends to only one test element.

6 Claims, 8 Drawing Figures

MULTI-ANALYTE TEST DEVICE

(1) Field of the Invention

The invention relates to a device and method useful in the clinical analysis of analytes of a liquid.

(2) Background of the Invention

A new approach to clinical analysis is described in U.S. Pat. No. 3,992,158, issued on Nov. 16, 1976. In one embodiment, a dry test element pre-incorporates all the necessary reagents for an extremely accurate quantitative radiometric assay on a single, small drop of liquid, such as blood serum. More specifically, the test element is provided with one or more reagent layers, and in fluid contact therewith, a spreading layer. A preferred isotropically porous spreading layer insures that a uniform concentration of the dissolved or dispersed substances of the test liquid arrives at the reagent layers for the necessary chemical reactions. The result is a uniform generation of a detectable response predictably related to the concentration of the analyte under study.

It was the practice when using such test elements to provide one element for the assay of glucose, another for the assay of blood urea nitrogen (BUN), aand so forth. Only one analyte was studied per each test element. One reason was that two different assay reactions combined into the same test element could very easily interfere with each other. E.g., the colorimetric density of one reaction in some instances overlapped the wavelengths of detection of another, thus masking out the other. In other instances, a reagent necessary for one reaction could be detrimental to another reaction. Therefore, in most cases it was not possible to use more than one radiometric assay in a single test element. Or, six separate tests usually required six separate test elements and six separate drops of liquid (blood serum in most cases).

The above-described system provided a marked improvement in the state of the art, because of the elimination of the plumbing required for "wet" techniques, and the improvement in accuracy. However, there remained the desire to provide a multi-analyte analysis within a single test device, using a single drop of liquid. Because of the problems noted above, this desire remained largely unfulfilled prior to this invention.

Prior to this invention, test strips have been provided wherein two different test compositions are present in the same device adjacent a capillary flow path for the liquid sample. For example, in U.S. Pat. No. 3,715,192, issued Feb. 6, 1973, FIG. 9, a dip and read element is described as having two different reagent layers spaced from each other to define a path through which the liquid sample flows. The disadvantage of devices of this type is that any reagent from one layer is free to flow into the other layer along the common flow path, thus providing potential contamination. Although such a disadvantage may be ignored in qualitative devices, it cannot be ignored when making exact, quantitative measurements.

(3) Related Applications

My U.S. application Ser. No. 954,689, filed on Oct. 25, 1978, entitled "Liquid Transport Device and Method", now U.S. Pat. No. 4,233,029, describes generically the use of opposed transport surfaces to distribute a liquid drop by capillary action to a plurality of test areas.

My U.S. application Ser. No. 059,816, filed on July 23, 1979, entitled "Electrode-Containing Device With Capillary Transport Between Electrodes", describes the use of opposed transport surfaces having capillary flow between them, as a means for carrying one or more drops of liquid to electrodes for potentiometric assays. In such assays, the reagents cannot readily diffuse out of the electrodes and contamination between reagents is not a problem. Accordingly no safeguards against such contamination are necessary.

SUMMARY OF THE INVENTION

In accord with the present invention there are advantageously featured a multi-analyte test device and method which facilitate radiometric assay of a plurality of different analytes of a single quantity of liquid.

In a related aspect of the invention such a device carries out the assays while preventing contamination between the various reagents used.

The aforesaid features are achieved by a multi-analyte test device for the analysis of a plurality of analytes in a liquid, the device comprising, a first member, a second covering member, the members having opposing surfaces, and means for spacing the members apart a distance effective to induce capillary flow of liquid introduced between the surfaces and to thus create a liquid transport zone. One of the members and the spacing means include, at a first location, access means permitting introduction of a quantity of the liquid into the zone. A plurality of individual test elements are disposed on one of the members at locations other than the first location and spaced away from the other of the members, at least two of the elements each respectively comprising a test composition for the generation of a detectable response indicative of a different one of the analytes. Control means confine liquid flow from the access means to a plurality of predetermined flow paths each of which extends to only one of the test elements, whereby all of the analytes from a single quantity of liquid are each detectable by the respective test element for that analyte without contamination from others of the test elements.

Such a device permits a plurality of analytes to be analyzed by the steps of introducing a quantity of liquid into the access means and detecting each of said responses after they develop.

Other features and advantages will become apparent upon reference to the following "Description of the Preferred Embodiments", when read in light of the attached drawings.

DESCRIPTION OF THE PREFERRED EMBODIMENTS

The device and method of this invention are described in connection with certain preferred embodiments as a device and method for analyzing blood serum. In addition, they can be applied to the radiometric detection of analytes of other liquids, for example, industrial liquids.

Figure 1:
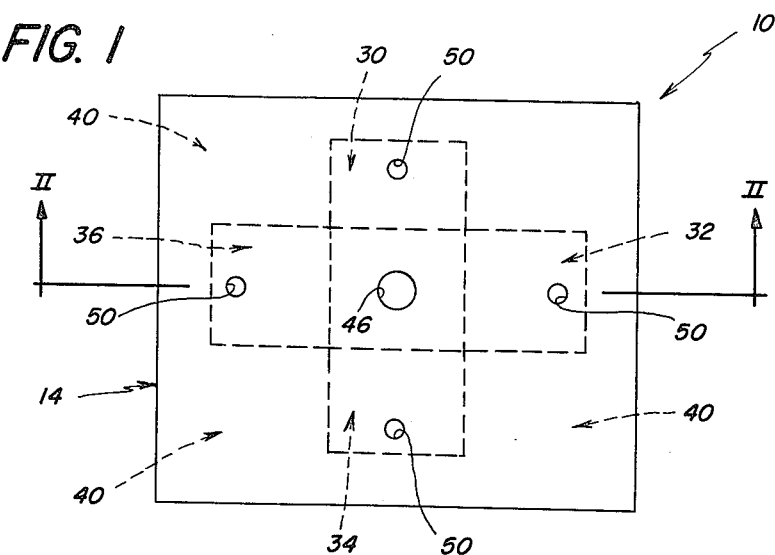
FIG. 1 is a plan view of a test device prepared in accordance with the invention.
Figure 2:
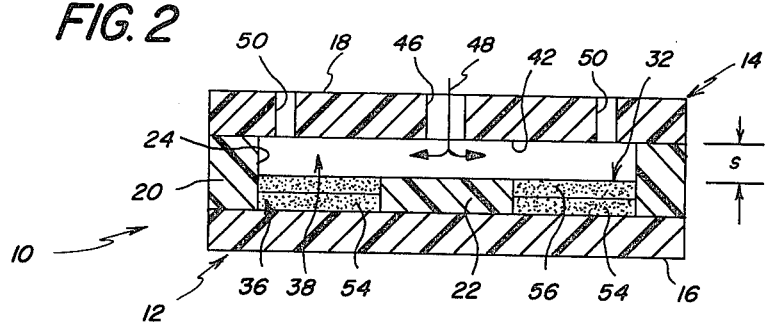
FIG. 2 is a sectional view taken generally along the plane of the line II—II of FIG. 1.

A device 10 constructed in accordance with one embodiment of the invention comprises, FIGS. 1 and 2, a preferably transparent support member 12 and a cover member 14 which have exterior surfaces 16 and 18, respectively. Members 12 and 14 are sealed at their peripheries to an intermediate member 20, FIG. 2, the sealing being effected by an appropriate, conventional adhesive, by ultrasonic welding, or the like. Except for the apertures discussed hereinafter, the chamber or zone formed between members 12, 14 and 20 is preferably airtight.

At the center of the interior surface of support member 12 is disposed a boss 22 which, together with the interior wall 24 of member 20, define a plurality of cavities extending radially from the boss. These cavities are filled with a plurality of individual test elements 30, 32, 34 and 36, FIG. 1, each of which contains all the reagents necessary for the detection of a different one of the several analytes expected to be present in the test liquid. Any portions of the cavities not filled with test elements, such as corners 40, can be occupied by a plastic spacer of the same composition as boss 22.

The top surfaces of elements 30, 32, 34 and 36, as well as that of the boss, are spaced a distance "s" from the interior surface 42 of cover member 14, FIG. 2. This distance is effective to induce capillary flow of liquid introduced between the cover member and either the boss 22 or the test elements and to thus create a liquid transport zone 38. Preferably "s" is between about 25 microns and about 500 microns. To permit the introduction of the test liquid, an access aperture 46 is formed in cover member 14 and functions as a receiving zone. Alternatively, the access aperture can be provided in the center portion of member 12 through boss 22. The size and shape of such aperture is such as to accommodate a drop of test liquid while at the same time insuring that the drop will contact both surface 42 and the boss 22. Because of the capillary spacing s, such contact immediately causes the drop to spread under the influence of capillary attraction. Although the shape of the wall defining access aperture 46 is not critical, and can be cylindrical as shown, shapes such as a regular hexagon, not shown, provide interior corners that act to center the drop within the aperture. To prevent cross-contamination of the reagents from the test elements, aperture 46 is disposed at a location different from that immediately adjacent any test element.

For a 10 μl sized drop, a convenient size of such a hexagonally shaped access aperture is one in which the outside diameter is about 0.26 cm. The corners of the hexagon should be as sharply defined as possible, and in no case have a radius of curvature greater than about 0.4 mm.

As the liquid advances as per arrows 48, FIG. 2, between surface 42 and the exterior surfaces of boss 22 and the test elements, the trapped air must exit. To provide a vent means for the trapped air, vent apertures 50 are formed in cover member 14 almost at the edge of zone 38 as defined by intermediate member 20. Each test element 30, 32, 34 and 36 has a vent aperture 50 disposed above it.

As in any confined volume, liquid flow can occur only in the direction in which the trapped air is being expelled. Thus, in accordance with one aspect of the invention, the access aperture 46, a portion of zone 38, and the apertures 50 confine the liquid to flow along a plurality of predetermined controlled flow paths, FIG. 3, such that each of the test elements 30, 32, 34 and 36 is operatively disposed in liquid alignment with only one of those paths. The paths are identified as $52^I$, $52^{II}$, $52^{III}$, and $52^{IV}$, respectively, leading from aperture 46 to the vent aperture 50 associated with that test element. It is this construction that prevents significant contamination of each test element by a reagent of another test element, inasmuch as flow proceeds to test elements 30, 32, 34 and 36, rather than between them.

In accordance with another aspect of the invention, each of the test elements 30, 32, 34 and 36 comprises one or more layers that are more or less absorbent of the liquid under test. Such absorbency further prevents cross-flow between test elements such as would create contamination. That is, as the sample liquid is absorbed, connective paths are removed between test elements that might otherwise remain after overall flow has ceased. Diffusion through quiescent liquid in the zone 38 is thus prevented.

Preferably each test element 30, 32, 34, and 36 comprises one or more reagent layers 54, FIG. 2, having a variety of binder compositions. For example, gelatin, cellulose acetate butyrate, polyvinyl alcohol, agarose and the like can be used, the degree of hydrophilicity of the layer 54 depending upon the material selected.

Additional layers such as a layer 56 can be disposed above layer 54 to provide a variety of chemistries or functions. For example, these can provide, either in layer 56 alone or together with layer 54, a reagent composition. Filtering, registration and mordanting functions can be provided also by such additional layers, such as are described in U.S. Pat. No. 4,042,335, issued on Aug. 16, 1977. Thus, layer 56 can comprise a reagent such as an enzyme, and a binder.

As used herein, "reagent" in "reagent composition" means a material that is capable of interaction with an analyte, a precursor of an analyte, a decomposition product of an analyte, or an intermediate. Thus, one of the reagents can be a preformed, radiometrically detectable species that is caused by the analyte of choice to move out of a radiometrically opaque portion or layer of the element, such as layer 56, into a radiometrically transparent portion or layer, such as a registration layer which can be layer 54.

The noted interaction between the reagents of the reagent composition and the analyte is therefore meant to refer to chemical reaction, catalytic activity as in the formation of an enzyme-substrate complex, or any other form of chemical or physical interaction, including physical displacement, that can produce ultimately a detectable response in the test element. The assay of the element is designed to produce a response signal that is predictably related to the amount of analyte that is present.

The preferred device is designed for a radiometric detection of the response, that is, by impinging electromagnetic excitation energy on the test elements. The response is then measured, preferably radiometrically. As is well known, radiometric detection includes both colorimetric and fluorimetric detection, depending upon the indicator reagent selected for the assay.

Alternatively, the device of the invention can be used with test elements having any kind of detectable response, the device being suitably modified, if necessary, to permit such alternate form of detection.

Each of the test elements 30, 32, 34 and 36 can test for a different analyte. Preferably, the assays are all oxygen-independent, as the flow of blood or blood serum into zone 38 tends to seal off the elements from any additional oxygen. Typical analytes which can be tested include BUN, total protein, bilirubin and the like. The necessary reagents and binder or vehicle compositions for, e.g., layers 54 and 56 of the elements can be, e.g., those described in, respectively, for these analytes, U.S. Pat. Nos. 4,066,403, issued on Jan. 3, 1978; 4,132,528, issued on Jan. 2, 1979; and 4,069,016 or 4,069,017, issued on Jan. 17, 1978. Thus, test element 30 can be designed to test for BUN, element 32 to test for total protein, element 34 to test for bilirubin, and element 36 to test for a fourth analyte. Alternatively, element 36 can be a duplicate of any of elements 30, 32 or 34 to provide a confirming reading, or it can be a blank to permit standardization of the analyzer.

As is apparent from the preceding, the quantity of liquid preferably is added to aperture 46 and zone 38 in the form of a drop. Alternatively, other forms of liquid introduction can be used.

Quantitative detection of the response produced in each test element by the analyte is preferably made, after a suitable development period, by scanning the device 10 through member 12 with a photometer or fluorimeter. Either a reflective or a transmissive mode can be used, depending upon the presence or absence of an opacifier in layer 56. A variety of such instruments can be used, for example the radiometer disclosed in U.S. Pat. No. 4,152,390, issued May 1, 1979, or the photometer described in U.S. Pat. No. 4,119,381, issued on Oct. 10, 1978. Of course, such instruments would be adapted to separately read each test element of device 10, such as through the use of filters and means to index the scanning beam to each test element. After detection, the device 10 is discarded.

Preferred materials for members 12, 14 and 20 are non-fibrous plastics that are substantially impervious to aqueous liquids. Examples include acetates, polystyrene, polyethylene, ABS plastic and polycarbonate.

Any other radial design can be used besides that of FIG. 1, to provide, e.g., 3, 5, 6 or n-test elements that are preferably equidistant from access aperture 46.

As an additional alternative, test elements 30, 32, 34 and 36 can be located on cover member 14 instead of member 12, or on both of said members, in suitably formed cavities therein.

Figure 4:
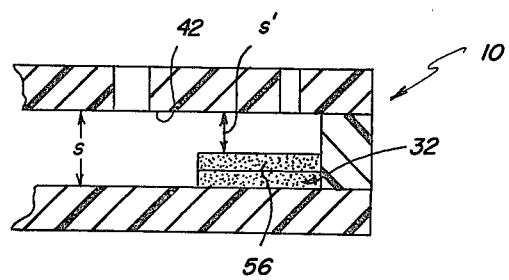
FIG. 4 is a fragmentary sectional view similar to that of FIG. 2, but illustrating an alternate embodiment.

The embodiment of FIG. 4 is the same as described above, except that the central boss has been omitted from device 10. In such an arrangement, the capillary spacing s is of course measured at the greatest spacing, it being noted that a space s' still exists between surface 42 and layer 56 of element 32. In this embodiment physical separation of the elements 30, 32, 34 and 36 aids in preventing cross contamination.

Figure 3:
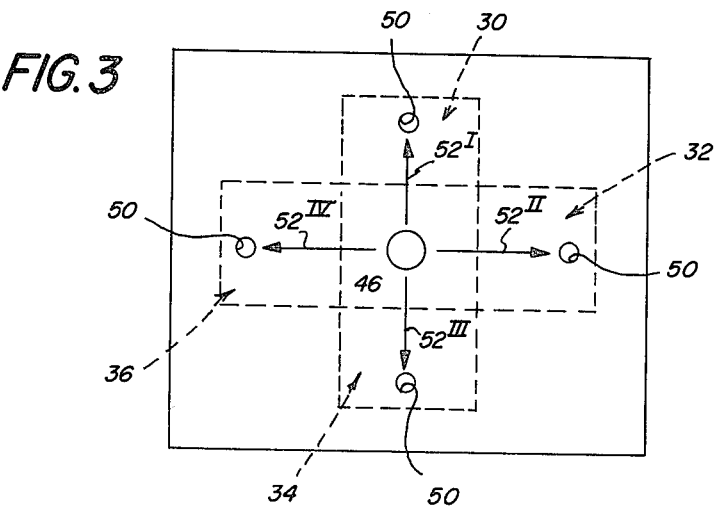
FIG. 3 is a plan view similar to that of FIG. 1, but illustrating the liquid flow paths to each test element.
Figure 5:
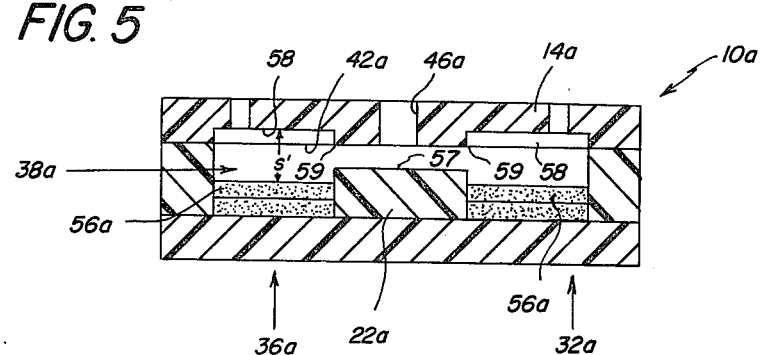
FIG. 5 is a sectional view similar to that of FIG. 2, illustrating yet another embodiment.

The embodiment of FIG. 5 is a preferred form of the embodiment illustrated in FIGS. 1–3. In some instances, it is possible for the initial liquid flow over boss 22 to inadvertently proceed to only one or two of the test elements 30, 32, 34 and 36 due to the non-directional nature of the surface of boss 22. That is, a smooth, non-directional boss surface could accidentally result in exclusive flow to only one side, and 1 test element, of the test device. If such is the case, device 10a should be used to alleviate the problem. Parts similar to those previously described bear the same reference numeral to which the distinguishing suffix "a" is added.

Thus, device 10a is identical to the device of FIG. 2 in that a plurality of test elements, of which only elements 36a and 32a are shown, are disposed about boss 22a, all of which have exterior surfaces spaced a capillary distance from surface 42a of cover member 14a which is apertured at 46a. However, to insure that incoming liquid first completely wets all of the surface of boss 22a, and then proceeds to all of the test elements, the following modifications are provided. Surface 57 of boss 22a is raised above the exterior surface of layers 56a, the reverse of the relation shown in FIG. 2. In addition, surface 42a is recessed slightly at portions 58 which are disposed directly opposite to elements 32a, 36a, etc. However, distance "s'" between the recessed portions of surface 42a and the exterior surface of layer 56a is still a capillary spacing, although larger than the spacing existing over boss 22a. This embodiment is effective because the first portion of the liquid that enters zone 38a "sees" a temporary energy barrier at the edges of surface 57 and the edges 59 in surface 42a created by the recesses. The meniscus prefers to fill the zone directly above boss surface 57, rather than proceed into the wider spacing denoted as "s'". After the zone directly above surface 57 is filled, however, the pressure of the incoming liquid overcomes the temporary energy barrier, and the liquid proceeds to fill the zone above all the test elements.

Figure 6:
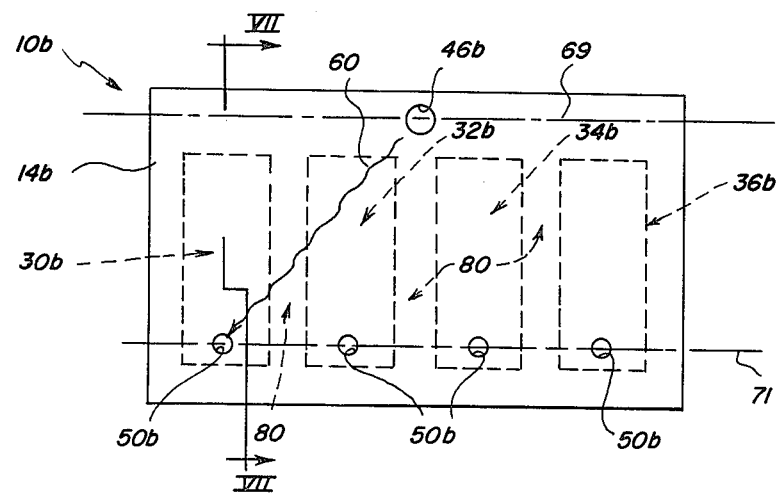
FIG. 6 is a plan view of still another embodiment.
Figure 7:
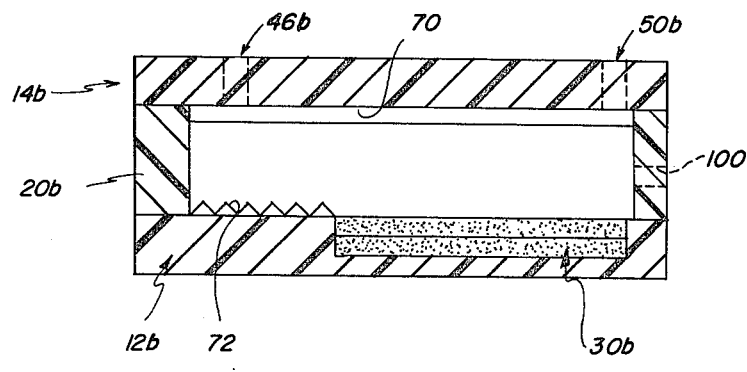
FIG. 7 is a secional view taken generally along the plane of the line VII—VII of FIG. 6.
Figure 8:
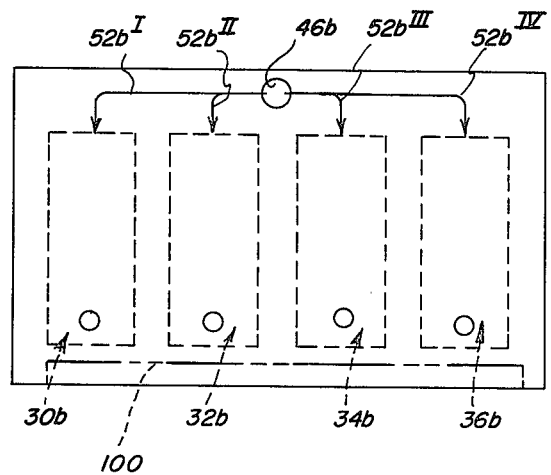
FIG. 8 is a plan view similar to that of FIG. 6, but illustrating the controlled liquid flow paths provided to each test element.

The interior surface of the cover member need not be smooth as shown in FIG. 2. In accordance with yet another aspect of the invention, control of the liquid flow paths can also be obtained by portions of one or both opposed surfaces having a plurality of exposed grooves. Such an embodiment is illustrated in FIGS. 6–8, wherein parts similar to those previously described bear the same reference numeral to which the distinguishing suffix "b" is appended. Thus, device 10b comprises a support member 12b, a cover member 14b and an intermediate member 20b that secures the two together as described previously. In this embodiment, test elements 30b, 32b, 34b and 36b are recessed into appropriately shaped cavities of support member 12b. A vent aperture 50b is located at an end of each test element opposite to the element end adjacent access aperture 46b.

Unlike the previously described embodiment, the test elements are not disposed equidistant from access aperture 46b, but rather are all to one side thereof. In such an arrangement, a flow path 60, FIG. 6, from aperture 46b to, say aperture 50b for element 30b, would be in fluid contact with more than one test element. Such a path would likely contaminate element 30b with reagents from element 32b. Therefore, the controlled flow of the liquid must proceed *in*directly to each test element, in the manner depicted by arrows $52b^I$, $52b^{II}$, $52b^{III}$, and $52b^{IV}$, FIG. 8. Flow *between* elements 30b, 32b, etc., is to be avoided to avoid contamination.

A preferred construction to provide such controlled flow is one in which the interior surface of member 14b is grooved, FIG. 7. Such grooves 70 are preferably parallel and linear, extending from a plane of intersection extending through aperture 46b, line 69, FIG. 6, generally perpendicularly to the linear row of apertures 50b delineated by line 71. In turn, the exposed surface portions of member 12b that oppose grooves 70 are also grooved at 72, but at an angle to grooves 70. Preferably, that angle is about 90°.

The grooves 70 and 72 can have a variety of shapes, including sawtooth, truncated and sinusoidal shapes. The pitch of the grooves can be constant or variable. The groove dimensions can also be varied, so long as capillary flow is maintained between the surfaces. A representative set of grooves for use with blood serum comprises a set of sawtooth grooves in which the width of a groove, and of the ridge that forms it, is in each case about 13 microns, and the depth of the grooves is about 7 microns.

To prevent contamination between elements, preferably no grooves 72 are included in those portions 80 of the member 12b that lie between test elements. If further protection of each test element is desired, a separation wall, not shown, can be included along portions 80.

The two sets of grooves angled with respect to each other control the flow pattern of the liquid as it advances from aperture 46b. More specifically, the advancing edges of the liquid appear to take on the shape of the edges of the grooves across which the liquid is moving. The groove edges in this embodiment extend rectilinearly. Thus the liquid appears to expand as a rectangle away from aperture 46b within zone 38b, until it reaches member 20b. It continues to move within grooves 72 towards the farther test elements 30b and 36b. At the same time, grooves 70 carry the liquid flow to the entrance portions of the test elements. The net effect is an apparent flow that follows the paths 52b¹ etc, FIG. 8, so that the liquid turns corners as necessary to provide flow to the test elements without flowing in significant amounts from one test element to another.

Because of the additional flow control provided by grooves 70 and 72, the embodiment of FIGS. 6-8 need not provide a capillary zone that is as airtight as the zones of the previous embodiments.

Yet another alternative is to provide, as the air vent means, one or more slots 100 in intermediate member 20b, shown in phantom in FIGS. 7 and 8, in place of air vents 50b. If one continuous slot 100 is used, FIG. 8, then the portion adjacent each of the test elements constitutes the air vent for that particular test element.

Still another alternative, not shown, is to form the access aperture in member 20b adjacent grooves 72, rather than in cover member 14b.

It will be readily appreciated that an additional series of test elements (not shown) can be arranged in a row on the opposite side of aperture 46b, to create a device having an axis of symmetry along line 69.

The invention has been described in detail with particular reference to certain preferred embodiments thereof, but it will be understood that variations and modifications can be effected within the spirit and scope of the invention.

What is claimed is:

1. A multi-analyte test device for the analysis of a plurality of analytes in a liquid, the device comprising, a first member,
a second covering member, said members having opposing surfaces,
means for spacing said members apart a distance effective to induce capillary flow of liquid introduced between said surfaces and to create a liquid transport zone,
at a first location, access means permitting introduction of a quantity of liquid into said zone, said access means being in either said first or second members or said spacing means, said first or second member opposite to said access means being configured to create a temporary energy barrier to liquid flow beyond the vicinity of said access means;
a plurality of individual test elements disposed on one of said members at locations other than said first location and spaced away from the other of said members, said other member in the areas directly opposite to said test elements being recessed, at least two of said elements each respectively comprising a test composition for the generation of a detectable response indicative of a different one of the analytes, and
control means for confining liquid flow from said access means to a plurality of predetermined flow paths each of which extends to only one of said test elements,
whereby all of said analytes from a single quantity of the liquid are each detectable by the respective test element for that analyte without contamination from others of said test elements.

2. A multi-analyte test device for the analysis of a plurality of analytes in a liquid, the device comprising, a first member,
a second covering member, said members having opposing surfaces,
means for spacing said members apart a distance effective to induce capillary flow of liquid introduced between said surfaces and to create a liquid transport zone,
at a first location, access means permitting introduction of a quantity of liquid into said zone, said access means being in either said first or said second member, the portion of said second or first of said members generally opposite to said access means being a non-test area;
a plurality of individual test elements disposed on said opposite member around said non-test area and spaced away from the other of said members, at least two of said elements each respectively comprising a test composition for the generation of a detectable response indicative of a different one of the analytes, and
control means for confining liquid flow from said access means to a plurality of predetermined flow paths each of which extends to only one of said test elements, said control means including means for preventing introduced liquid from flowing onto said test elements until after said non-test area is completely wetted.

3. A device as defined in claim 2, wherein said control means includes a plurality of vent means for venting air from said zone ahead of advancing liquid, a vent means being associated with each of said test elements.

4. A device as defined in claim 1 or 2, wherein said test elements each comprise an absorbent layer containing at least one reagent, and said test compositions react with the analytes of the liquid to generate a radiometrically detectable response.

5. A device as defined in claim 1 or 2, wherein said each test element includes all the reagents necessary for a radiometric assay of a particular analyte.

6. A device as defined in claim 1 or 2, wherein said two elements include, respectively, the reagents necessary for the detection in said elements of total protein and blood urea nitrogen.

* * * * *